(12) United States Patent
Shin

(10) Patent No.: US 10,156,227 B2
(45) Date of Patent: *Dec. 18, 2018

(54) ELECTRO-OSMOTIC PUMP USING REVERSIBLE ELECTRODE REACTION AND FLUID PUMPING SYSTEM USING SAME

(71) Applicant: SOGANG UNIVERSITY RESEARCH FOUNDATION, Seoul (KR)

(72) Inventor: Woonsup Shin, Seoul (KR)

(73) Assignee: Sogang University Research Foundation, Seoul (KR)

( * ) Notice: Subject to any disclaimer, the term of this patent is extended or adjusted under 35 U.S.C. 154(b) by 239 days.

This patent is subject to a terminal disclaimer.

(21) Appl. No.: 14/761,063

(22) PCT Filed: Dec. 18, 2013

(86) PCT No.: PCT/KR2013/011801
§ 371 (c)(1),
(2) Date: Jul. 15, 2015

(87) PCT Pub. No.: WO2014/112726
PCT Pub. Date: Jul. 24, 2014

(65) Prior Publication Data
US 2016/0025083 A1   Jan. 28, 2016

(30) Foreign Application Priority Data

Jan. 15, 2013 (KR) .................. 10-2013-0004361
Jul. 30, 2013 (KR) .................. 10-2013-0090234

(51) Int. Cl.
*F04B 17/00* (2006.01)
*F04B 19/00* (2006.01)
(Continued)

(52) U.S. Cl.
CPC .......... *F04B 17/003* (2013.01); *A61K 9/0004* (2013.01); *F04B 19/006* (2013.01);
(Continued)

(58) Field of Classification Search
CPC ......... A61M 2005/14204; A61M 2005/14513; A61M 5/142; A61M 5/145; F04B 17/03;
(Continued)

(56) References Cited

U.S. PATENT DOCUMENTS

2005/0230080 A1* 10/2005 Paul ...................... F04B 19/006
165/47
2008/0260542 A1* 10/2008 Nishikawa .............. B01L 3/565
417/48

(Continued)

FOREIGN PATENT DOCUMENTS

CN   101213457 A   7/2008
CN   101427368 A   5/2009
(Continued)

OTHER PUBLICATIONS

Office Action dated Jun. 2, 2016 for CN Application No. 201380074754.5 with English translation (12 pages).

*Primary Examiner* — Dominick L Plakkoottam
(74) *Attorney, Agent, or Firm* — Fox Rothschild LLP

(57) ABSTRACT

An electro-osmotic pump using a reversible electrode reaction is provided, the electro-osmotic pump using a reversible electrode reaction comprising: a membrane that allows movement of a fluid; and first and second electrodes that are arranged on both sides of the membrane, respectively, and composed of a porous material or structure to allow the movement of the fluid, and a material to cause a reversible electrochemical reaction, wherein the first and second electrodes are alternately and reversely supplied with a voltage to make the electrochemical reaction repeat alternately for- (Continued)

ward and backward, and as a result, the alternate change of the movement direction of the fluid generates a pumping force to repair the first and second electrodes.

7 Claims, 12 Drawing Sheets

(51) Int. Cl.
 *F04B 43/067* (2006.01)
 *A61K 9/00* (2006.01)
(52) U.S. Cl.
 CPC ....... *F04B 43/067* (2013.01); *B01L 2200/027* (2013.01); *B01L 2400/0418* (2013.01); *Y10T 137/2218* (2015.04)
(58) Field of Classification Search
 CPC ................. F04B 19/006; B01D 61/427; Y10T 137/2213; A61K 9/0004
 See application file for complete search history.

(56) References Cited

U.S. PATENT DOCUMENTS

| | | | | |
|---|---|---|---|---|
| 2009/0126813 | A1* | 5/2009 | Yanagisawa | F04B 19/006 137/831 |
| 2009/0260990 | A1* | 10/2009 | Yanagisawa | C04B 35/14 204/641 |
| 2010/0328841 | A1* | 12/2010 | Reinhoudt | C02F 1/46109 361/301.4 |
| 2011/0168558 | A1* | 7/2011 | Fransaer | C09D 5/024 204/477 |
| 2013/0041353 | A1* | 2/2013 | Shin | A61M 5/14248 604/892.1 |
| 2013/0153797 | A1* | 6/2013 | Puleo | B01L 3/50273 251/12 |
| 2013/0156615 | A1* | 6/2013 | Puleo | A61K 9/0004 417/410.1 |
| 2013/0276851 | A1* | 10/2013 | Crispin | H01L 35/28 136/201 |

FOREIGN PATENT DOCUMENTS

| | | |
|---|---|---|
| CN | 101971086 A | 2/2011 |
| CN | 102753470 A | 10/2012 |
| EP | 1511885 | 3/2006 |
| JP | 2001240730 | 9/2001 |
| JP | 2003112182 | 4/2003 |
| KR | 20100350602 | 1/2003 |
| WO | 2004048644 | 6/2004 |
| WO | 2011112723 | 9/2011 |
| WO | 2012124415 A1 | 9/2012 |

* cited by examiner

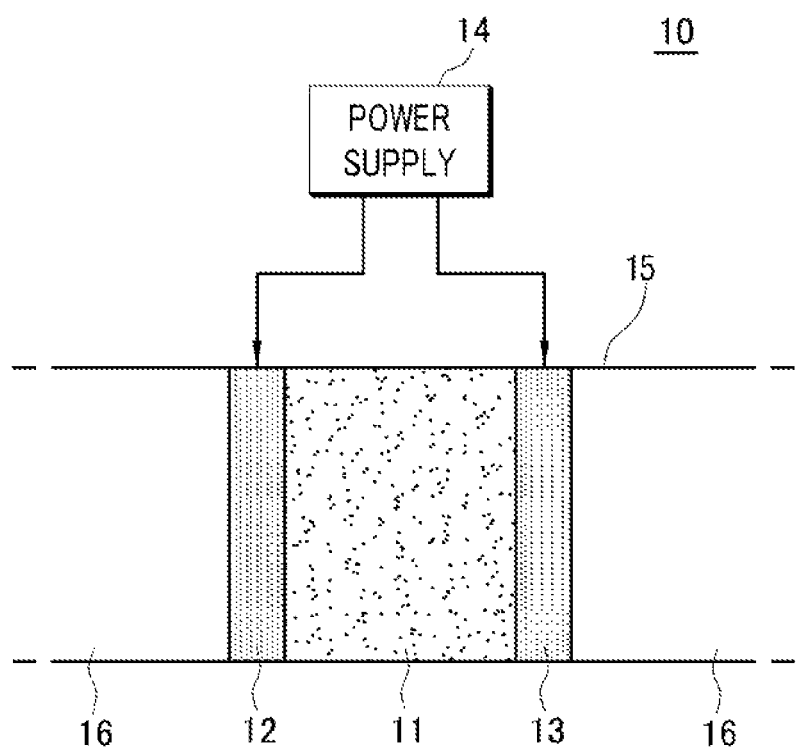

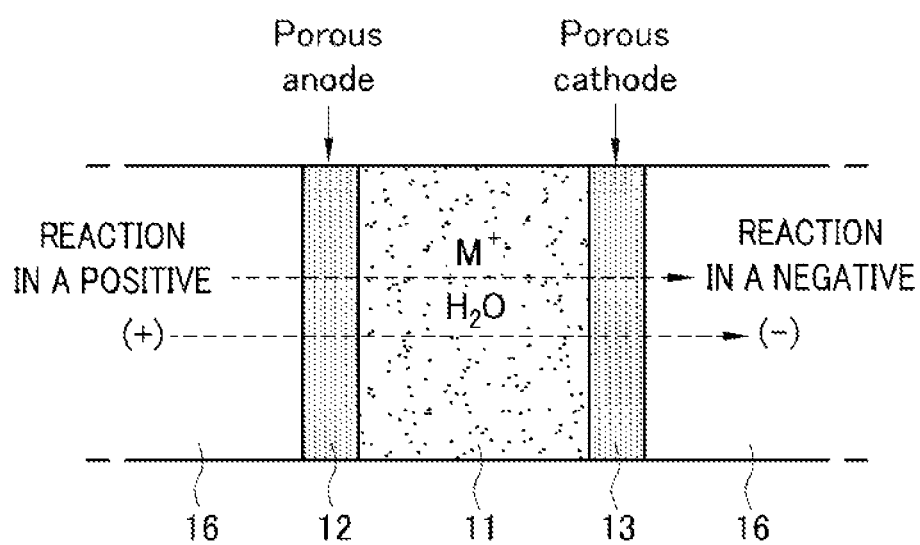

ELECTRO-OSMOTIC PUMP USING REVERSIBLE ELECTRODE REACTION AND FLUID PUMPING SYSTEM USING SAME

CROSS-REFERENCE TO RELATED APPLICATION

This application is a US National Phase of International Application PCT/KR2013/011801, filed Dec. 18, 2013, which claims the benefit of Korea Patent Application No. 10-2013-0004361, filed Jan. 15, 2013 and Korea Patent Application No. 10-2013-0090234, filed Jul. 30, 2013, the disclosures of all of which are incorporated herein by reference.

TECHNICAL FIELD

The embodiments described herein pertain generally to an electro-osmotic pump, more particularly, an electro-osmotic pump using a reversible electrode reaction and a fluid pumping system using the same.

BACKGROUND ART

An electro-osmotic pump is a pump using the principle that a fluid moves due to electro-osmosis occurring when a voltage is applied to both ends of a capillary or a porous membrane by using electrodes, and unlike ordinary pumps, the electro-osmotic pump is advantageous in that it causes no noise since it has no part that mechanically operates, and can effectively control a flow rate in proportion to the voltage applied.

A conventional electro-osmotic pump uses chemically stable platinum as an electrode material. When an aqueous solution is used as a fluid, a reaction in a positive (+) pole is as shown in Reaction Formula 1 below, and a reaction in a negative (−) pole is as shown in Reaction Formula 2 below.

$2H_2O \rightarrow O_2 + 4H^+ + 4e^-$ [Reaction Formula 1]

$2H_2O + 2e^- \rightarrow H_2 + 2OH^-$ [Reaction Formula 2]

According to Reaction Formula 1, an oxygen gas resulting from an oxidization reaction of water is continuously generated in the positive (+) pole; and according to Reaction Formula 2, a hydrogen gas resulting from a reduction reaction of water is continuously generated in the negative (−) pole.

The movement of electrons and ions as a result of the oxidization reaction and the reduction reaction is an essential phenomenon to continuously move a fluid in the electro-osmotic pump. When the electro-osmotic pump is embodied by using the platinum electrode as described above, there is difficulty in practically using the pump since it is difficult to realize a stable flow rate due to the phenomenon that the gas generated by the oxidization and reduction reactions is caught in small pores of a porous membrane, and it is difficult to realize closed-loop due to a safety problem causing from the simultaneous and continuous generation of the oxygen gas and the hydrogen gas within the fluid.

Further, in case of the electro-osmotic pump using the platinum electrode, since water of the moving fluid participates in the oxidization and reduction reactions, and the platinum as an electrode material does not participate in the reactions and is only used as an electrode causing the oxidization and reduction reactions of water, the electrode is maintained. In this case, the platinum electrode is called a non-consumable electrode. The electro-osmotic pump, which stably and safely operates without generating gas, can be achieved if an electrode material is made by using a reaction that generates no gas. For example, in case of using a silver/silver oxide electrode reaction, a reaction in the positive (+) pole is as shown in Reaction Formula 3 below, and a reaction in the negative (−) pole is as shown in Reaction Formula 4 below.

$2Ag(s) + H_2O \rightarrow Ag_2O(s) + 2H^+ 2e^-$ [Reaction Formula 3]

$Ag_2O(s) + 2H^+ 2e^- \rightarrow 2Ag(s)$ [Reaction Formula 4]

In the positive (+) pole, an oxidization reaction of silver according to Reaction Formula 3 occurs, and in the negative (−) pole, a reduction reaction of a silver oxide according to Reaction Formula 4 occurs. In this case, the electrode acts as a material participating in the electrode reactions, rather than a means for simply applying a voltage. If this consumable electrode is applied to the electro-osmotic pump, a volume of a fluid that can be moved by the electro-osmotic pump is restricted due to the limited amount of the electrode material.

Therefore, it is impossible to safely and stably move a large volume of a fluid without generating gas for a long period of time by using the conventional electro-osmotic pump. In other words, the electro-osmotic pump, to which the consumable electrode reaction is applied, has had a problem in that due to a limited amount of an electrode active material, the pump is suitable for moving a small volume of a fluid in one direction one time by means of an electrode reaction that can be realized with the small value of the fluid, but is not suitable for continuously moving a large volume of a fluid.

DISCLOSURE OF THE INVENTION

Problems to be Solved by the Invention

In order to solve the foregoing problems, an objective of the present disclosure is to enable an electro-osmotic pump to move a large volume of a fluid while maintaining its size and structure without generating gas for a prolonged time, and enable electrodes to be repaired by a reversible reaction so as to increase usability of the electro-osmotic pump. Other objectives of the present disclosure can be easily understood through descriptions of embodiments below.

Means for Solving the Problems

In order to achieve the above-described objectives, an aspect of the present disclosure provides an electro-osmotic pump using a reversible electrode reaction, comprising: a membrane that allows movement of a fluid; and first and second electrodes that are arranged on both sides of the membrane, respectively, and composed of a porous material or structure to allow the movement of the fluid, and a material to cause a reversible electrochemical reaction, wherein the first and second electrodes are alternately and reversely supplied with a voltage to make the electrochemical reaction repeat alternately forward and backward, and as a result, the alternate change of the movement direction of the fluid generates a pumping force to repair the first and second electrodes.

Also, further comprising a fluid passageway that provides a movement passageway of a fluid moving in both sides of the pump, sandwiching the membrane and the first and second electrodes.

Also, wherein the fluid passageway consists of first and second hollow caps attached to the first and second electrodes, respectively, and the first and second caps are provided with connection parts for connection of a tube.

Also, wherein first and second contact strips made of a conducting material are inserted into outer peripheral surfaces of the first and second electrodes, respectively.

Also, wherein the first or second electrode is a material capable of generating a monovalent cation through a reversible electrochemical reaction.

Also, wherein the first or second electrode comprises any one of Ag/Ag2O, MnO(OH), and polyaniline (PANI).

Also, wherein the first or second electrode comprises one or more of a metal oxide, a polymer, and metal hexacyanoferrate.

Also, wherein the metal oxide comprises one or more species selected from the group consisting of a molybdenum oxide (MoO3), a tungsten oxide (WO3), a cerium oxide (CeO2), and polyoxometalate.

Also, wherein the polymer comprises one or more species selected from the group consisting of polythiophene, a derivative of polythiophene, polypyrrole, a derivative of polypyrrole, polythionine, and a quinone polymer.

Also, wherein the metal hexacyanoferrate comprises one or more species selected from the group consisting of prussian blue, iron hexacyanoferrate (FeHCF), copper hexacyanoferrate (CuHCF), and cobalt hexacyanoferrate (CoHCF).

Another aspect of the present disclosure provides a fluid pumping system, comprising: an electro-osmotic pump comprising: a membrane that allows movement of a fluid; first and second electrodes that are arranged on both sides of the membrane, respectively, and composed of a porous material or structure to allow the movement of the fluid and a material to cause a reversible electrochemical reaction; and a power supply that alternately and reversely supplies a voltage to the first and second electrodes, to provide a pumping force to a transfer target fluid; and a separator that is provided in at least one end of the electro-osmotic pump to separate the fluid and the transfer target fluid from each other, wherein the first and second electrodes are alternately and reversely supplied with a voltage to make the electrochemical reaction repeat alternately forward and backward, and as a result, a suction force and a discharge force are repeatedly delivered to the transfer target fluid through the separator due to the repeated forward and backward movement of the fluid.

Also, wherein the electro-osmotic pump comprises a fluid passageway that provides a movement passageway of the fluid moving in both sides of the pump, sandwiching the membrane and the first and second electrodes. And wherein the fluid passageway comprises a first hollow cap attached to the first electrode and a second hollow cap attached to the second electrode.

Also, further comprising: a first contact strip that is inserted into an outer peripheral surface of the first electrode; and a second contact strip that is inserted into an outer peripheral surface of the second electrode.

Also, wherein either the first or second electrode generates a monovalent cation through the reversible electrochemical reaction, and the other consumes a monovalent cation.

Also, wherein the first and second electrodes comprise any one of Ag/Ag2O, MnO(OH), and polyaniline (PANI).

Also, wherein the first and second electrodes comprise one or more of a metal oxide, a polymer, and metal hexacyanoferrate.

Also, wherein the metal oxide comprises one or more species selected from the group consisting of a molybdenum oxide (MoO3), a tungsten oxide (WO3), a cerium oxide (CeO2), and polyoxometalate.

Also, wherein the polymer comprises one or more species selected from the group consisting of polythiophene, a derivative of polythiophene, polypyrrole, a derivative of polypyrrole, polythionine, and a quinone polymer.

Also, wherein the metal hexacyanoferrate comprises one or more species selected from the group consisting of prussian blue, iron hexacyanoferrate (FeHCF), copper hexacyanoferrate (CuHCF), and cobalt hexacyanoferrate (CoHCF).

Also, wherein the separator comprises one of a diaphragm, a polymer film, and a slider.

Effect of the Invention

With the electro-osmotic pump using the reversible reaction and the fluid pumping system using the same in accordance with the present disclosure, it is possible to enable the electro-osmotic pump to move a large volume of a fluid while maintaining its size and structure for a long period of time, and enable the electrodes to be repaired by the reversible reaction, so as to improve the usability of the electro-osmotic pump without generating gas.

BRIEF DESCRIPTION OF THE DRAWINGS

FIG. 1 is a structural view illustrating an electro-osmotic pump using a reversible electrode reaction in accordance with a first embodiment.

FIG. 2A and FIG. 2B depicts an operation of the electro-osmotic pump using the reversible electrode reaction in accordance with the first embodiment.

DETAILED DESCRIPTION

Figure 2B:
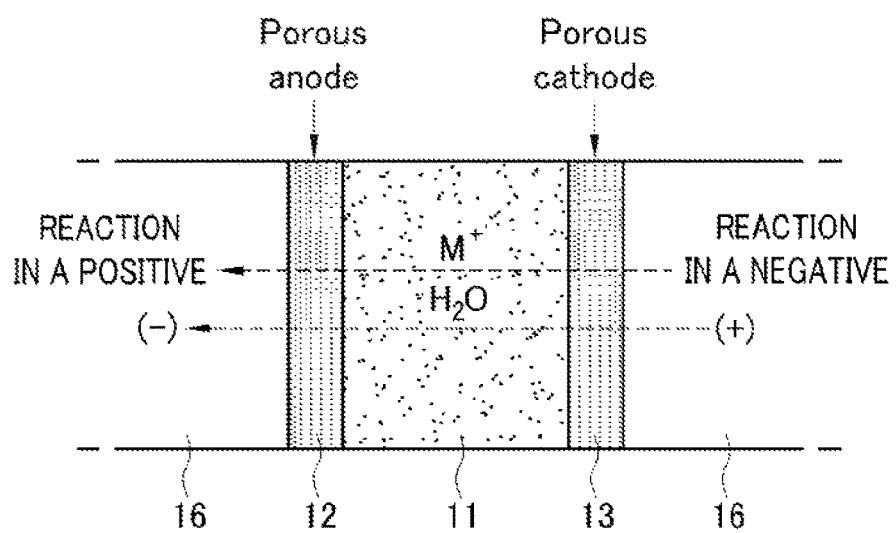

As the present disclosure may be subject to various modifications and have various embodiments, specific embodiments are illustrated in the drawings and described in detail. However, the illustrations and the descriptions are not intended to limit the present disclosure to the specific embodiments, and should be construed as including any modifications, equivalents or substitutes, which fall within the technical concept and scope of the present disclosure. The present disclosure may be variously modified, and the scope of the present disclosure is not limited to the embodiments described below.

Hereinafter, embodiments of the present disclosure are described in detail with reference to the accompanying drawings. Components, which are identical or correspond to one another irrespective of drawing reference numerals, are denoted by an identical reference numeral, and overlapping descriptions in this regard are omitted.

FIG. 1 is a structural view illustrating an electro-osmotic pump using a reversible electrode reaction in accordance with a first embodiment.

Referring to FIG. 1, an electro-osmotic pump 10 using a reversible electrode reaction in accordance with an embodiment may include a membrane 11, and first and second electrodes 12, 13.

The membrane 11 allows movement of a fluid 16, and is provided between the first and second electrodes 12, 13 to maintain the space between the first and second electrodes 12, 13, and furthermore, allow movement of a fluid, ions, etc. In addition, the membrane 11 may be, for example, a disk membrane prepared by using silica composed of a granular material in a size of 1 to 5 µm, and as another example, the membrane 11 may be composed of a porous material or structure. These materials are merely examples and are not limited thereto, and the membrane 11 may be made in various forms by using various materials and construct a membrane electrode assembly (MEA) structure together with the first and second electrodes 12, 13.

The first and second electrodes 12, 13 are arranged on both sides of the membrane 11, respectively, and composed of a porous material or structure to allow the movement of the fluid 16 and a material to cause a reversible electrochemical reaction, e.g., a material for generating or consuming a monovalent cation such as $H^+$, $Na^+$ and $K^+$ through the reversible electrochemical reaction. Accordingly, the first and second electrodes 12, 13 are alternately and reversely supplied with a voltage by means of a power supply 14 so as to make the electrochemical reaction of the first and second electrodes 12, 13 repeat forward and backward so that the alternate change of the moving direction of the fluid 16 generates a pumping force, and the first and second electrodes 12, 13 are repaired by the electrochemical reaction in the forward and backward directions.

The power supply 14 alternately and reversely supplies a voltage to the first and second electrodes 12, 13, and to this end, the power supply 14 may include a DC supply device that supplies an external or internal power as a DC power to the first and second electrodes 12, 13, and a voltage direction switching device that allows the DC voltage supplied from the DC supply device to be alternately and reversely supplied every set time. Here, the description that the power supply 14 alternately and reversely supplies a voltage may include reversely supplying currents. Accordingly, a voltage is reversely supplied to the first and second electrodes 12, 13 by the power supply 14 to make the electrochemical reaction by the first and second electrodes 12, 13 repeat forward and backward, and thereby, providing the pumping force generated by the change of the flow of the fluid 16.

The first or second electrode 12, 13 may include any one of $Ag/Ag_2O$, $MnO(OH)$, and polyaniline (PANI). In addition, the first or second electrode 12, 13 may include any one of a metal oxide, a polymer, and metal hexacyanoferrate, or a composite of a combination selected therefrom, wherein the metal oxide may include part selected from or all of a molybdenum oxide ($MoO_3$), a tungsten oxide ($WO_3$), a cerium oxide ($CeO_2$), and polyoxometalate, the polymer may include part selected from or all of polythiophene, a derivative of polythiophene, polypyrrole, a derivative of polypyrrole, polythionine, and a quinone polymer, and the metal hexacyanoferrate (HCF) may include part selected from or all of prussian blue, iron hexacyanoferrate (FeHCF), copper hexacyanoferrate (CuHCF), and cobalt hexacyanoferrate (CoHCF). In addition, the composite may be, for example, a composite of a metal oxide and a polymer.

Meanwhile, the electro-osmotic pump may further include a fluid passageway 15 that provides a movement passageway of the fluid 16 moving in both sides of the electro-osmotic pump, sandwiching the membrane 11 and the first and second electrodes 12, 13. Here, the fluid passageway 15 may be of a shape of a reservoir with its inside filled with the fluid 16, e.g., a cylindrical shape, but the shape of the fluid passageway 15 is not limited thereto and may include various shapes. In addition, the fluid 16 fills not only the fluid passageway 15 but also the porous membrane 11 and the first and second electrodes 12, 13, may be, for example, water, alcohol, an aqueous solution and a mixture solution thereof, and is not limited with regard to its type if it can be used as an operation fluid.

The fluid passageway 15 may have an opening (not illustrated) for delivery of the pumping force, and the opening is formed in one or both of the two (2) spaces divided by the membrane 11 and the first and second electrodes 12, 13 so as to provide the pumping force by the movement of the fluid 16 to the outside, and connected to the fluid pumping system 1 (illustrated in FIG. 5) as described later. Meanwhile, since the fluid 16 filling the inside of the fluid passageway 15 may be leaked to the outside due to the formation of the opening in the fluid passageway 15, a separator 70 (illustrated in FIG. 5), which is described later, may be provided in the opening. If a multiple number of openings are formed, the openings other than the opening provided with the separator 70 may be blocked by members such as pipes or caps. In addition, the opening of the fluid passageway 15 may be configured to be blocked by the providing of the separator, e.g., members for delivering the pumping force to the outside such as oil, diaphragms, polymer membranes, and sliders, and this configuration is also included in the technical concept of the present disclosure.

The electro-osmotic pump 10 using the reversible electrode reaction in accordance with the first embodiment may apply materials causing the reversible electrochemical reaction such as $Ag/Ag_2O$, polyaniline (PANI) and $MnO(OH)$ to both the first and second electrodes 12, 13, and continuously reverse voltages to be applied to both ends of the first and second electrodes 12, 13 by means of the power supply 14, so as to continuously transfer a transfer target fluid as much as a volume taken out by using two (2) check valves provided in the fluid pumping system 1 (illustrated in FIG. 5), which is described later.

Referring to FIG. 2A and FIG. 2B, in the electro-osmotic pump 10 using the reversible electrode reaction in accordance with the first embodiment, when the direction of the voltage applied to the first and second electrodes 12, 13 is switched to reverse the reaction occurring in the first and second electrodes 12, 13, the flow of the fluid 16 may be reversed. Here, since an aqueous solution is mostly used as the fluid 16, the fluid 16 is indicated as $H_2O$, and since the ions moving according to the electrode reaction may include various ions such as $H^+$, $Na^+$ and $K^+$, they are indicated as $M^+$ as a representative example.

Accordingly, in the case where the first and second electrodes 12, 13 use the electrode material causing the reversible electrode reaction, when the first and second electrodes 12, 13 are reversely supplied with a voltage, the direction of the flow of the fluid 16 is reversed, and also, the electrode reaction occurs in a reverse direction, so that the electrode active material consumed by a forward reaction when the fluid 16 flows in the forward direction may be restored to be in its original state. That is, when a voltage or currents as much as a charge amount used to move the fluid 16 in the forward direction are reversely supplied, the same volume of the fluid 16 as that of the fluid 16 moved in the forward direction may move in the reverse direction. For example, when a voltage corresponding to an amount of silver consumed by the oxidization reaction (Reaction Formula 5 below) of the silver in the positive (+) pole is reversely applied, the consumed amount of the silver may be reproduced by a reduction reaction (Reaction Formula 6 below) of a silver oxide, which is a reverse reaction of the oxidization reaction. The consumption and the reproduction may similarly occur in the negative (−) pole as well.

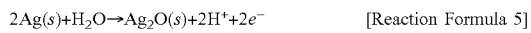
$$2Ag(s) + H_2O \rightarrow Ag_2O(s) + 2H^+ + 2e^- \qquad \text{[Reaction Formula 5]}$$

$$Ag_2O(s) + 2H^+ + 2e^- \rightarrow 2Ag(s) \qquad \text{[Reaction Formula 6]}$$

Figure 5:
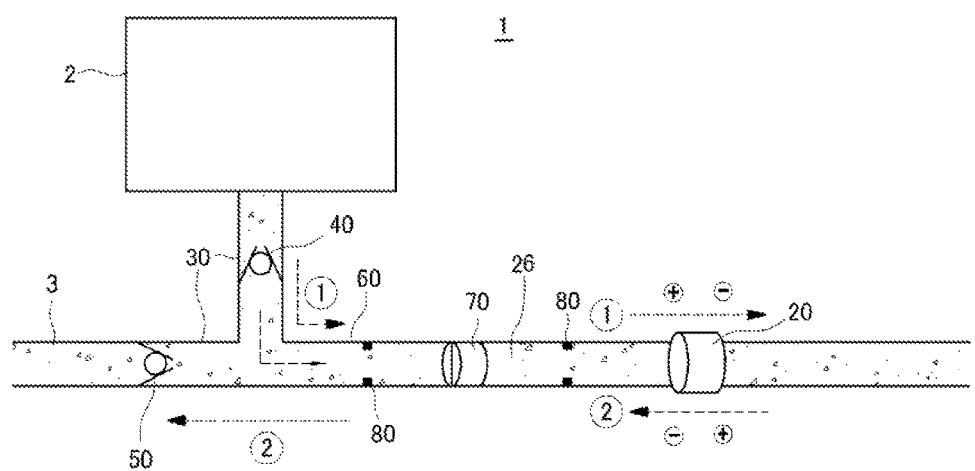
FIG. 5 is a structural view illustrating a fluid pumping system using a reversible electrode reaction in accordance with an embodiment.

The electro-osmotic pump 10 capable of switching the movement direction of the fluid 16 according to the direction of the voltage to be applied may enable continuous movement of the fluid in one direction by using two (2) check valves 40, 50 in the fluid pumping system 1 illustrated in FIG. 5. The check valves are intended to repeat suction and discharge, and since the electrode reaction occurring in each of the electrodes is the reversible reaction, in which the electrode reactions occur reversely, the electrode material used may be restored.

Figure 3:
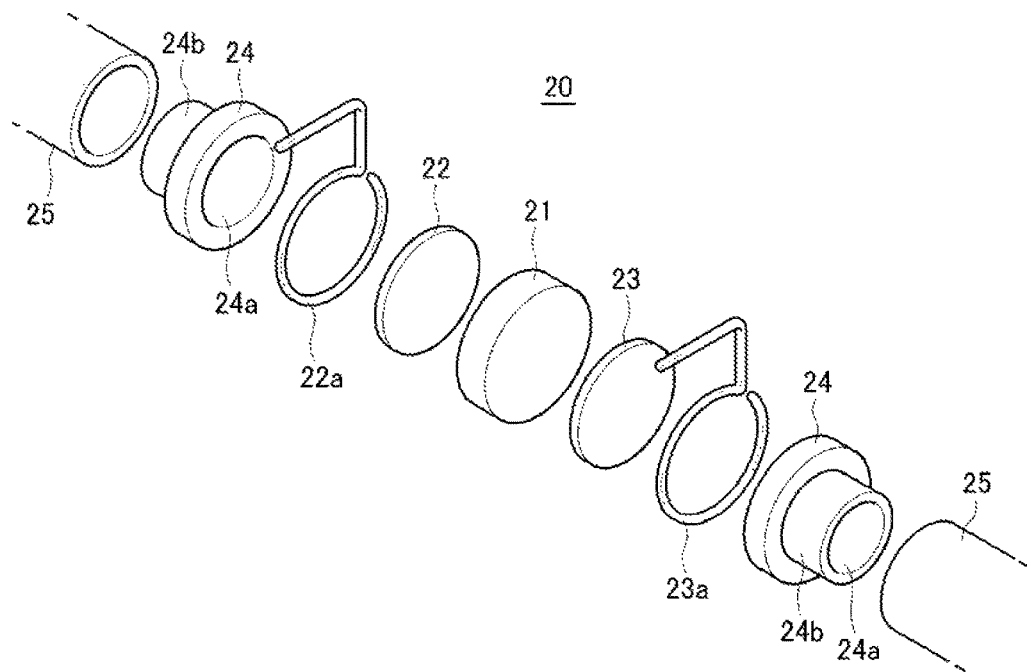
FIG. 3 is a disassembly view of an electro-osmotic pump using a reversible electrode reaction in accordance with a second embodiment.
Figure 4:
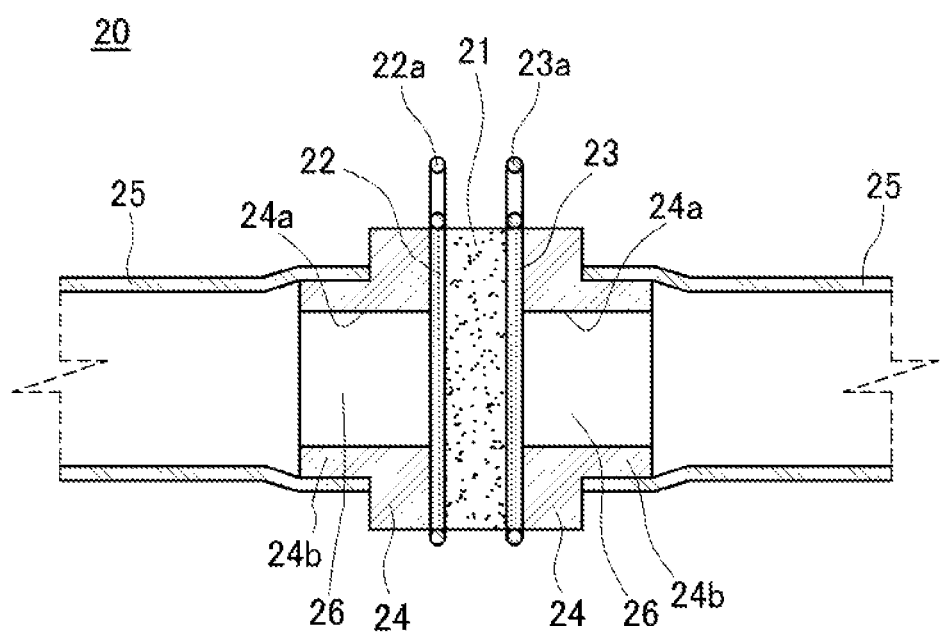
FIG. 4 is a cross-sectional view illustrating the electro-osmotic pump using the reversible electrode reaction in accordance with the second embodiment.

FIG. 3 is a disassembly view illustrating the electro-osmotic pump using the reversible electrode reaction in accordance with a second embodiment, and FIG. 4 is a cross-sectional view illustrating the electro-osmotic pump using the reversible electrode reaction in accordance with the second embodiment.

Referring to FIG. 3 and FIG. 4, the electro-osmotic pump 20 using the reversible electrode reaction in accordance with the second embodiment may include a membrane 21 that allows movement of a fluid 26, and first and second electrodes 22, 23 that are arranged on both sides of the membrane 21, respectively, and made of a porous material or structure to allow the movement of the fluid 26 and a material to cause a reversible electrochemical reaction, wherein the first and second electrodes 22, 23 are alternately and reversely supplied with a voltage so as to make the electrochemical reaction repeat alternately forward and backward so that the alternate change of the movement direction of the fluid 26 generates a pumping force to repair the first and second electrodes. Here, detailed descriptions of the specific structure and operation of the membrane 21 and the first and second electrodes 22, 23 will be omitted since the membrane 11 and the first and second electrodes 12, 13 of the electro-osmotic pump 10 using the reversible electrode reaction in accordance with the first embodiment have been described in detail, and the membrane 21 and the first and second electrodes 22, 23 will be described based on differences from the membrane 11 and the first and second electrodes 12, 13.

The membrane 21 and the first and second electrodes 22, 23 may be of a disk shape, and a coating material, a blocking sheet, or an adhesive sheet may be laminated in a direction of an outer peripheral surface of the membrane 21 and the first and second electrodes 22, 23 so as to suppress leakage of the fluid 26.

The electro-osmotic pump 20 may further include a fluid passageway that provides a movement passageway of the fluid 26 moving in both sides of the pump, sandwiching the membrane 21 and the first and second electrodes 22, 23, wherein the fluid passageway may be composed of, for example, first and second hollow caps 24 attached to the first and second electrodes 22, 23, respectively, by an adhesive, a joint member or the like, and the first and second caps 24 may be formed with hollows 24a, and provided with connection members 24b for connection of a tube 25. Here, the tube 25 may be a silicon tube or the like, and a pumping line 60 (illustrated in FIG. 5) of the fluid pumping system 1 (illustrated in FIG. 5). Instead of the first and second caps 24, O-rings like PVC may be used to be mounted in the tube 25 or others, or other connection members made of various materials and having various shapes may substitute the first and second caps 24.

First and second contact strips 22a, 23a made of a conducting material may be inserted into the outer peripheral surfaces of the first and second electrodes 22, 23, respectively. Here, the first and second contact strips 22a, 23a may be made of a conducting material like silver (Ag) or copper (Cu), and may be of a ring shape to be inserted into the outer peripheral surfaces of the first and second electrodes 22, 23.

FIG. 5 is a structural view illustrating a fluid pumping system using a reversible electrode reaction in accordance with an embodiment.

Referring to FIG. 5, the fluid pumping system 1 using a reversible electrode reaction in accordance with an Example may include a transfer line 30 that provides a passageway for transferring the transfer target fluid 3 from a reservoir 2 to the outside, first and second check valves 40, 50 that are provided being spaced from each other in the transfer line 30, and restrict the transfer target fluid 3 from being transferred in a direction reverse to a transfer direction, a pumping line 60 that is connected between the first and second check valves 40, 50 in the transfer line 30, an electro-osmotic pump 20 that is mounted in the pumping line 60 to provide a pumping force, and a separator 70 that is provided to separate the electro-osmotic pump 20 from the transfer target fluid 3 and transfer the pumping force of the electro-osmotic pump 20 to the transfer target fluid 3, wherein the fluid 26 used as an operation fluid may be any one of water, alcohol, and an aqueous solution or a mixture solution thereof, and the electro-osmotic pump 20 may be the electro-osmotic pump 20 using the reversible electrode reaction in accordance with the second embodiment.

Meanwhile, the fluid pumping system 1 using the reversible electrode reaction in this embodiment is an electro-osmotic pump, and will be described by referring to the electro-osmotic pump 20 using the reversible electrode reaction in accordance with the second embodiment as an example for the fluid pumping system 1. However, the fluid pumping system 1 is not limited to the electro-osmotic pump 20, and the electro-osmotic pump 10 using the reversible electrode reaction in accordance with the first embodiment may also be applied. Since the electro-osmotic pumps 10 and 20 have been described, overlapping descriptions in this regard are omitted hereinafter.

The transfer line 30 may be a pipe, a hose or the like, of which one end is connected to the reservoir 2 so as to enable transfer of the transfer target fluid 3, e.g., various fluids including drug, an aqueous solution, and an organic solution, from the reservoir 2 and made of a proper material according to the characteristic of the transfer target fluid 3.

The first and second check valves 40, 50 are provided being spaced from each other in the transfer line 60 to provide a space for connection of the pumping line 60, and enable the transfer target fluid 3 to be transferred only in one direction due to the pumping force of the electro-osmotic pump 20.

One end of the pumping line 60 is connected to the transfer line 30 so as to form, for example, a "T"-shaped connection structure together with the transfer line 30, and the other end thereof may be connected to a connection part 24b (illustrated in FIG. 3 and FIG. 4) of the hollow caps 24 (illustrated in FIG. 3 and FIG. 4) in the fluid passageway of the electro-osmotic pump 20. Meanwhile, the electro-osmotic pump 20 may be connected to one end of the pumping line 60, and as another example, both the sides of the electro-osmotic pump 20 may be connected onto the pumping line 60.

The separator 70 may be provided in the pumping line 60 to separate the two sides of the pumping line 60 from each other, and formed of oil to form an oil gap in the interior side of the pumping line 60, a diaphragm such as a rubber made of a thin film with elasticity or a metal plate, a polymer film, or a slider moving along the interior side of the pumping line 60. Besides, the separator 70 may be formed of various separating materials or members, and a stopper 80 may be provided in the interior side of the pumping line 60 such that when the separator 70 like oil or a slider moves along the interior side of the pumping line 60, the stopper restricts the movement distance.

The operation of the fluid pumping system 1 using the reversible electrode reaction in accordance with an embodiment is described more in detail.

The first check valve 40 may be provided close to the reservoir 2, and the second valve 50 may be provided close to the side, from which the transfer target fluid 3 is discharged for injection. The first check valve 40 allows the transfer target fluid 3 to flow from the reservoir 2 toward the electro-osmotic pump 20 (Direction $\hat{1}$), but does not allow the transfer target fluid 3 to flow in the opposite direction. In addition, the second check valve 50 allows the transfer target fluid 3 to flow toward the side, from which the transfer target fluid 3 is discharged for injection, (Direction $\hat{2}$), but does not allow the transfer target fluid 3 to flow in the opposite direction.

Based on FIG. 5, when a (+) voltage is applied to the left electrode (e.g., the first electrode 22, as illustrated in FIG. 4) of the electro-osmotic pump 20, and a (−) voltage is applied to the right electrode (e.g., the second electrode 23, as illustrated in FIG. 4) of the electro-osmotic pump 20, the movement of the fluid 26 occurs in Direction $\hat{1}$, and the transfer target fluid 3 to be injected from the reservoir 2 is sucked in the direction of the electro-osmotic pump 20. In this case, since the first check valve 40 is opened, and the second check valve 50 is closed, discharge for injecting the transfer target fluid 3 to the outside does not occur. Reversely, when a (−) voltage is applied to the left electrode (e.g., the first electrode 22, as illustrated in FIG. 4) of the electro-osmotic pump 20, and a (+) voltage is applied to the right electrode (e.g., the second electrode 23, as illustrated in FIG. 4) of the electro-osmotic pump 20, the movement of the fluid 26 occurs in the opposite direction, i.e., Direction Z, and the transfer target fluid 3 is discharged to be injected into a proper place. In this case, since the first check valve 40 is closed, and the second check valve 50 is opened, reverse flow of the transfer target fluid 3 toward the reservoir 2 may be suppressed. In addition, the fluid 26 and the transfer target fluid 3 are separated from each other by the separator 70 such that they are not in contact with each other.

Accordingly, when the suction and the discharge are repeated by the fluid pumping system 1, the transfer target fluid 3 in the reservoir 2 may be injected into a proper place even though the electro-osmotic pump 20 in a small scale is used. In addition, since the electrode reactions in the respective electrodes 22, 23 (illustrated in FIG. 4) reversely occur, i.e., the suction and the discharge, causing a reversible reaction, the used electrode material can be repaired, and thus, a discharge amount of the electrode material is restored, so that continuous driving becomes possible. Eventually, with the electro-osmotic pump 20 having a consumable electrode material having a specific discharge amount, the consumption and the repair of the electrode material are repeated, and the introduction and the discharge of the transfer target fluid 3 are repeated, so as to enable continuous movement of the large volume of the transfer target fluid 3, and the operation of the electro-osmotic pump 20 over lone time.

The cycle for repeating the suction and the discharge may be adjusted to range from several seconds to a few tens of minutes according to necessity. The operation of the fluid pumping system 1 has been described by referring to the electro-osmotic pump 20 using the reversible electrode reaction in accordance with the second embodiment, but the same principle as described above may be applied to the case where the electro-osmotic pump 10 using the reversible electrode reaction in accordance with the first embodiment is used.

Applicable examples for the electro-osmotic pump using the reversible electrode reaction and the fluid pumping system using the same in accordance with the embodiments are described.

1. In Case of Using an $Ag/Ag_2O$ Electrode

Figure 6:
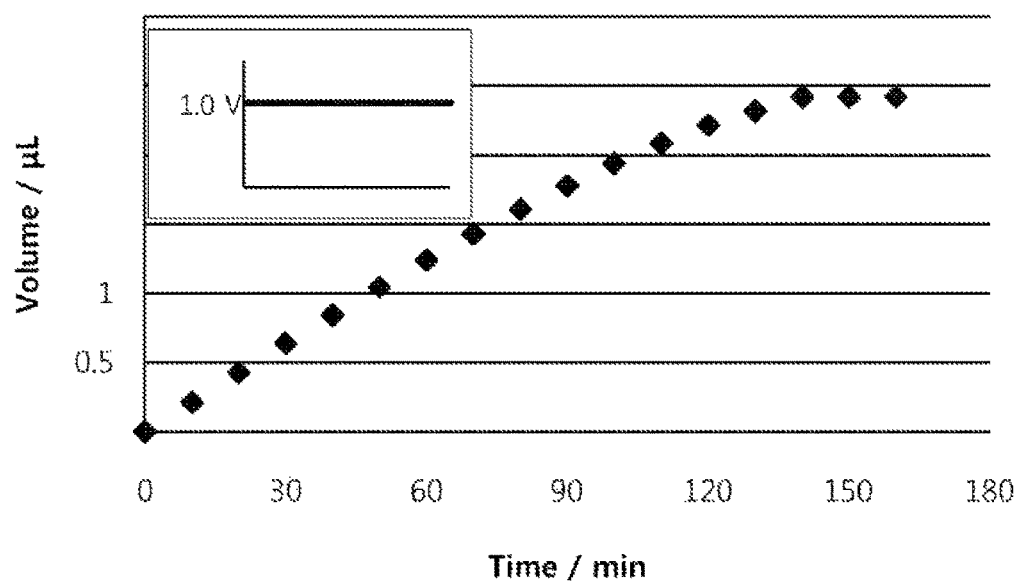
FIG. 6 to FIG. 11 depict operation of the electro-osmotic pump using the reversible electrode reaction and the fluid pumping system using the same in accordance with the present disclosure.
Figure 7:
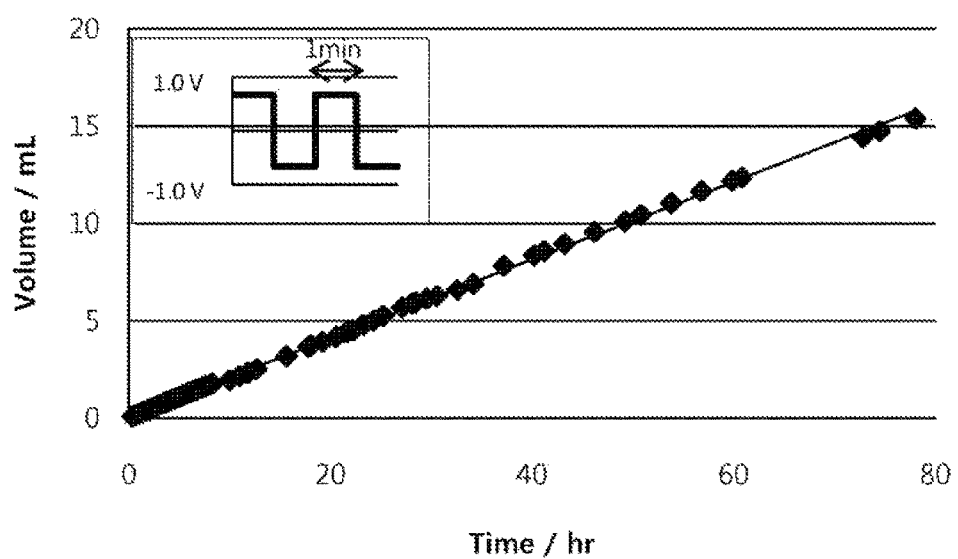

When structuring the electro-osmotic pump, a disk membrane made by using 1 to 5 μm silica and having a thickness of 2 mm and a diameter of 8 mm was used, and an electrode formed by electrodepositing 4.6 C silver (Ag) on a disk-shape porous carbon electrode with a diameter of 8 mm, and then, electrochemically oxidizing 2.3 C, which is a half of 4.6 C, to obtain a silver oxide ($Ag_2O$) was identically used for both positive (+) and negative (−) electrodes. As shown in FIG. 6, when the electro-osmotic pump was driven with a voltage of 1.0 V, a 2 ml transfer target fluid could be moved in one direction over about 3 hours. When the identically manufactured electro-osmotic pump was driven with the same voltage of 1.0 V while switching the direction of the voltage every one (1) minute, and the fluid pumping system illustrated in FIG. 5 was used, a 12 ml transfer target fluid could be moved for about 3 days.

The electrode reactions in the case of using the $Ag/Ag_2O$ electrode are as shown in Reaction Formulas 7 and 8 below.

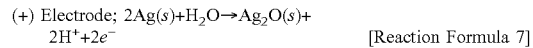

(+) Electrode: $2Ag(s)+H_2O \rightarrow Ag_2O(s)+2H^++2e^-$ [Reaction Formula 7]

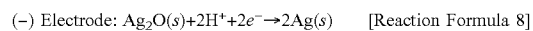

(−) Electrode: $Ag_2O(s)+2H^++2e^- \rightarrow 2Ag(s)$ [Reaction Formula 8]

2. In Case of Using a MnO(OH) Electrode

Figure 8:
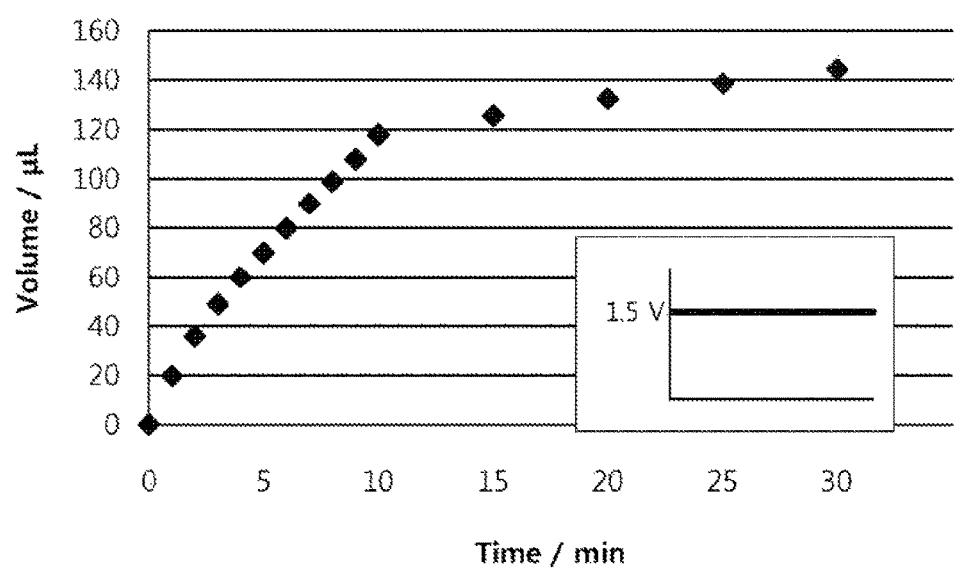
Figure 9:
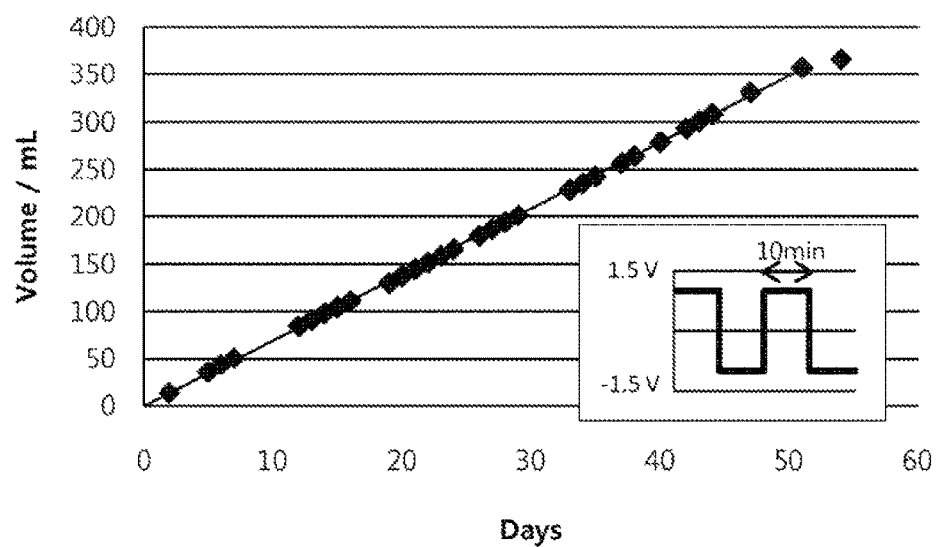

The structure of the electro-osmotic pump was the same as that in the case of using the $Ag/Ag_2O$ electrode, except that an electrode formed by electrodepositing 0.8 C MnO(OH), instead of $Ag/Ag_2O$, on the porous carbon electrode was identically used for both positive (+) and negative (−) poles. As shown in FIG. 8, when the electro-osmotic pump was driven in one direction with a voltage of 1.5 V, an about 20 μl/min flow rate was exhibited for initial 1 minute, and the flow rate decreased by about 10 minutes to reach about 10 μl/mm, and then, further decreased, so that the electro-osmotic pump was no longer driven. In case of using MnO(OH) as an electrode active material, when the electro-osmotic pump was driven in one direction, and the transfer target fluid flowed, a volume of the transfer target fluid that was moved for 10 minutes was merely 160 μl. When the electro-osmotic pump was driven while switching the direction of the voltage every ten (10) minutes by using the fluid pumping system illustrated in FIG. 5, the pumping was stably performed for 50 days, as shown in FIG. 9, and the volume of the transfer target fluid that was moved for the same period of time was about 350 ml.

The electrode reactions in the case of using the MnO(OH) electrode may be suggested as shown in Reaction Formulas 9 and 10 below.

(+) Electrode; MnO(OH)(s)→MnO$_2$(s)+ H$^+$+e$^-$            [Reaction Formula 9]

(−) Electrode; MnO$_2$(s)+H$^+$+e$^-$→ MnO(OH)(s)            [Reaction Formula 10]

The initial condition when the electrode is actually structured is believed to correspond to the state that MnO(OH)(s) and MnO$_2$(s) co-exist, and in this case, the reaction formulas may be represented by Reaction Formulas 11 and 12 below.

(+) Electrode; MnO(OH)(s)→MnO$_{1+\delta}$(OH)s+δH$^+$+ δe$^-$            [Reaction Formula 11]

(−) Electrode; MnO(OH)(s)+δH++δe$^+$→MnO$_{1-\delta}$ (OH)$_{1+\delta}$(s)            [Reaction Formula 12]

3. In Case of Using a Polyaniline (PANI) Electrode

Figure 10:
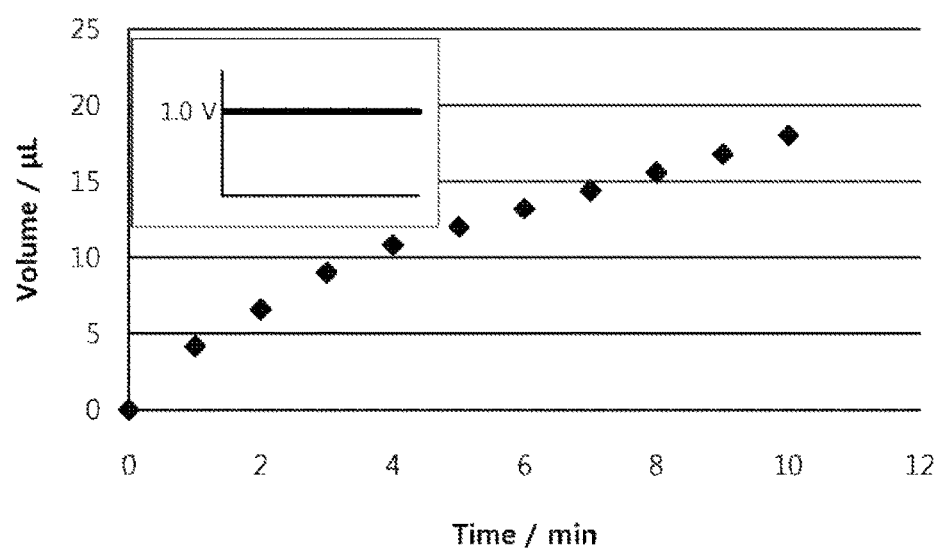
Figure 11:
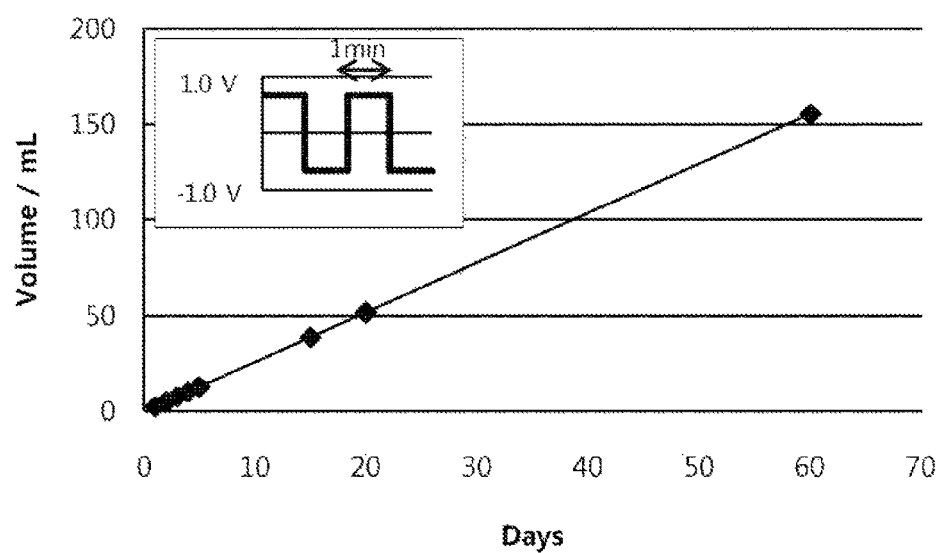

In this case, the structure of the electro-osmotic pump was the same as described above, except that an electrode obtained by electrodepositing a 30 mC small amount of polyaniline (PANI) on an 8 mm disk-shape porous carbon electrode was used. The electrodeposition was carried out by immersing the porous carbon electrode in a solution, in which 0.1 M aniline and 0.5M polystyrenesulfonic acid (PSSA) were mixed with each other, to undergo oxidative electrodeposition. In this case, the porous carbon electrode traveled back and forth within a zone of −0.2 to 1.2 V vis Ag/AgCl at 50 m V/s for 20 cycles. A conducting polymer produced by the electrodeposition was PANI-PSS, in which polystyrene sulfonate (PSS') was mixed into polyaniline. As shown in FIG. 10, when the electro-osmotic pump was driven in a forward direction with a voltage of 1.0 V, an about 5 pt/mm flow rate was exhibited for initial 1 minute, but rapidly decreased within a few minutes. A volume of the transfer target fluid that was moved by applying the voltage in one direction for 10 minutes was merely 20 μl. When the electro-osmotic pump was driven while switching the direction of the voltage every one (1) minute by using the fluid pumping system illustrated in FIG. 5, the pump stably operated for two (2) months or longer as shown in FIG. 11, and a volume of the transfer target fluid that was moved for the same period of time was 150 ml or more.

Polyaniline (PANI) carries out a redox reaction as shown in Reaction Formula 13 below in the condition that anions can freely move. Ions indicated by A' in Reaction Formula 13 are anions, and a type of the anions mixed into polyaniline varies depending on a condition for the solution, in which the redox reaction occurs. For example, when polyaniline is oxidized in an HCl solution, Cl$^-$ is mixed into a polymer to meet a charge balance. However, as suggested in the present embodiment, when polyaniline is made by the electrodeposition, if the solution includes an anionic polymer, i.e., polystyrene sulfonate (PSS'), PSS' is mixed into the solution to make PANI-PSS, and thus, PSS cannot move, so that a cation H$^+$ present in water is forced to move.

[Reaction Formula 13]

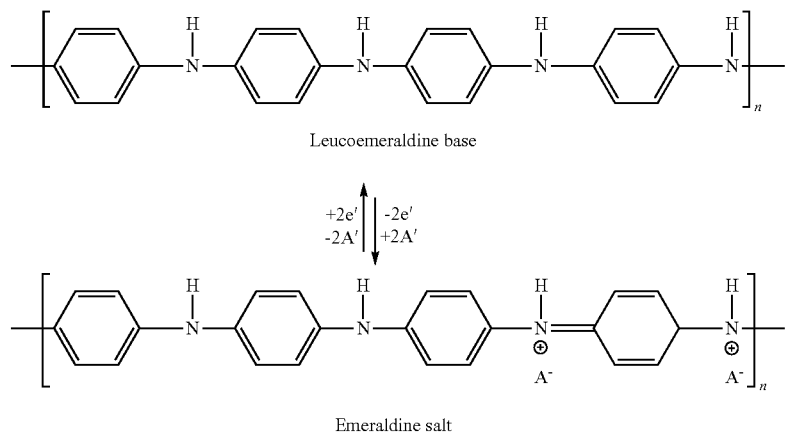

Leucoemeraldine base

Emeraldine salt

Therefore, when the PANI-PSS polymer in the oxidized form is illustrated by —[P$_n$-[S]$_n$, the electrode reactions in the electro-osmotic pump used in the present embodiment may be suggested by Reaction Formulas 14 and 15 below.

(+) Electrode; —(P)$_n$]-[SH]$_n$-→-[P$^+$]$_n$-[S-]$_n$-+nH$^+$+ ne$^-$            [Reaction Formula 14]

(−) Electrode: —[P$^+$]$_n$-[S']$_n$-+nH$^+$+ne$^-$→-[P]$_n$— [SH]$_n^-$

With respect to the condition for the electrode reactions in the electro-osmotic pumps 10, 20 using the reversible electrode reaction in accordance with the embodiments, it is preferable that a reversible electrode reaction can occur, both oxidized species and reduced species stably exist, and oxidation and reduction reactions accompany movement of ions, and especially, the reaction accompanying movement of H$^+$ includes all proton coupled electron transfer reactions (PCET), which are widely known in the field of nature and common chemical reactions.

In accordance with the embodiments, it is possible to enable the electro-osmotic pump to move a large volume of a fluid while maintaining its size and structure for a long period of time, enable electrodes to be repaired by a reversible reaction, and increase the usability of the electro-osmotic pump without generating gas.

The present disclosure has been described with reference to the accompanying drawings, but it is natural that various modifications and changes may be made to the present disclosure within the technical concept of the present disclosure. Therefore, the scope of the present disclosure

I claim:

1. A fluid pumping system, comprising:
an electro-osmotic pump comprising: a membrane that allows movement of a fluid; first and second electrodes that are arranged on both sides of the membrane, respectively, and composed of a porous material or structure to allow the movement of the fluid and a material to cause a reversible electrochemical reaction; and a power supply that alternately and reversely supplies a voltage to the first and second electrodes, to provide a pumping force to a transfer target fluid;
a separator that is provided in at least one end of the electro-osmotic pump to separate the fluid and the transfer target fluid from each other;
a first valve provided near a first end of a transfer line that is connected to a transfer target fluid source;
a second valve provided near a second end of the transfer line that is connected to the outside of the fluid pumping system; and
a pumping line that is branched from the transfer line between the first and second valves to be connected to the electro-osmotic pump and delivers the pumping force to the transfer line,
wherein the first and second electrodes are alternately and reversely supplied with a voltage to make the electrochemical reaction repeat alternately forward and backward, and as a result, a suction force and a discharge force are repeatedly delivered to the transfer target fluid through the separator due to the repeated forward and backward movement of the fluid, and
wherein the first and second valves are opened and closed to allow or restrict the flow of the transfer target fluid.

2. The fluid pumping system of claim 1,
wherein the electrochemical reaction is repeated alternately in the forward direction and the backward direction to repeat consumption and restore the capacity of each of the first and second electrodes, and maintain the original state of the electrodes.

3. The fluid pumping system of claim 1,
wherein the power supply comprises:
a DC supply device that supplies a DC voltage to each of the first and second electrodes; and
a voltage direction switching device that alternately and reversely switches the DC voltage supplied to each of the first and second electrodes every set time.

4. The fluid pumping system of claim 1,
wherein the opening and the closing of the first and second valves are operated reversely.

5. The fluid pumping system of claim 1,
wherein the first and second valves are check valves,
wherein when the suction force is delivered to the transfer target fluid, the first valve is opened, and the second valve is closed,
wherein when the discharge force is delivered to the transfer target fluid, the first valve is closed, and the second valve is opened.

6. The fluid pumping system of claim 1, further comprising
a first stopper and a second stopper that are provided to restrict a movement distance of the separator, when the separator moves due to the movement of the fluid,
wherein the first stopper is provided at one side of the separator and the second stopper is provided at the other side of the separator.

7. The fluid pumping system of claim 1,
wherein the separator comprises one of a diaphragm, a polymer film, and a slider.

* * * * *